United States Patent [19]

Kleiman et al.

[11] 3,961,033

[45] June 1, 1976

[54] PREPARATION OF BROMINE

[75] Inventors: Joseph P. Kleiman, Birmingham; Kestutis A. Keblys, Southfield, both of Mich.

[73] Assignee: Ethyl Corporation, Richmond, Va.

[22] Filed: Mar. 6, 1975

[21] Appl. No.: 555,801

[52] U.S. Cl. .............................. 423/502; 260/658 R
[51] Int. Cl.² ........................................... C01B 7/00
[58] Field of Search ........................... 423/500, 502; 260/658 R, 654 H, 654 R, 659 R

[56] References Cited
UNITED STATES PATENTS

| | | | |
|---|---|---|---|
| 3,370,096 | 2/1968 | Donaldson | 260/658 R |
| 3,607,958 | 9/1971 | Forman | 260/658 R |

FOREIGN PATENTS OR APPLICATIONS

| | | | |
|---|---|---|---|
| 2,045,644 | 5/1972 | Germany | 423/500 |

OTHER PUBLICATIONS

Abridgement of Patent Specification 18,012; Government Printer, Israel Program For Scientific Translations.

Calingaert, G., et al.; Journal of American Chemical Society, June, 1940 pp. 1545–1547.

Olah, G.; Friedal–Crafts and Related Reactions, vol. I., Interscience Publishers (1963) pp. 205–210, 297–298, 587–588.

*Primary Examiner*—L. Dewayne Rutledge
*Assistant Examiner*—Michael L. Lewis
*Attorney, Agent, or Firm*—Donald L. Johnson; John F. Sieberth; Robert A. Linn

[57] ABSTRACT

Bromine is produced by reacting chlorine and ethylene dibromide in the presence of an aluminum halide catalyst, e.g. aluminum chloride. A small amount of bromine present prior to chlorine addition shortens the induction period. Some decomposition of the organic product occurs if it is distilled in the presence of aluminum-containing residues. These residues can be removed by water wash which can be followed by drying with $H_2SO_4$. After such treatment, ethylene dichloride can be recovered by distillation without substantial decomposition.

14 Claims, 1 Drawing Figure

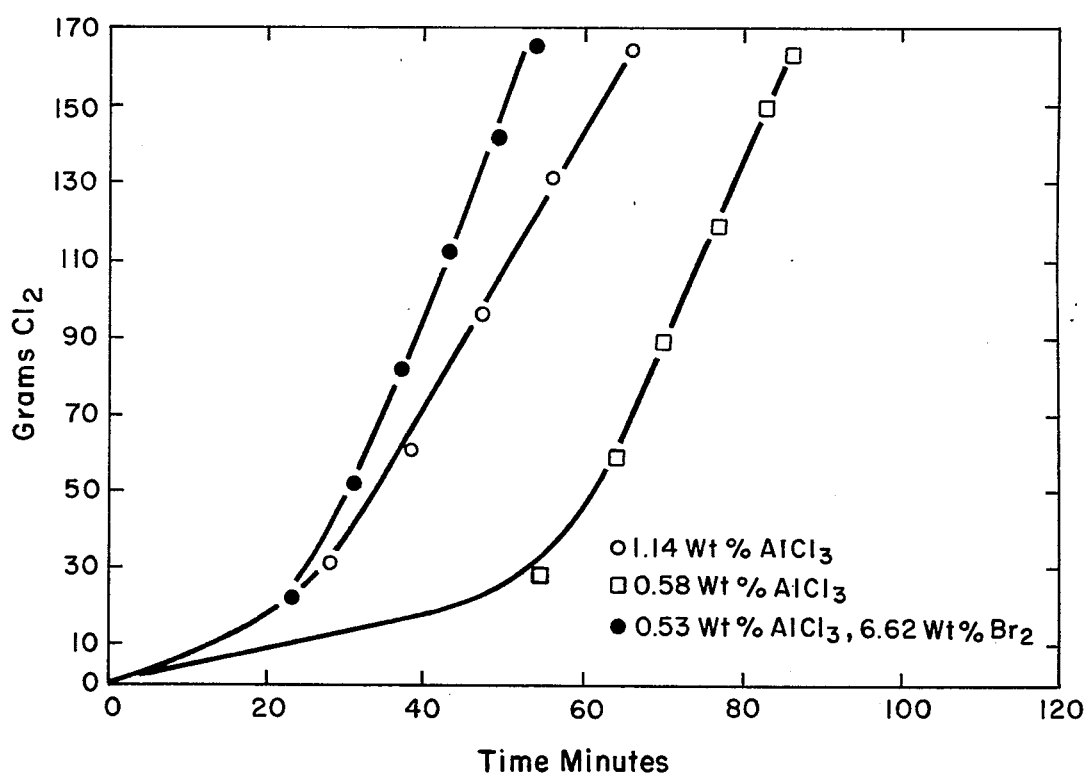

PREPARATION OF BROMINE

BACKGROUND OF THE INVENTION

Because bromine is corrosive, its storage and shipment requires special vessels and precautions. This invention pertains to means for recovering bromine from ethylene dibromide, a compound that is readily stored and shipped. The reaction employed to recover bromine is simple to carry out and requires common reactants.

Israeli Pat. No. 17898 is directed to bromine recovery. It markedly differs from the present process in (1) specifying a bromoalkane having either two bromines linked to the same carbon or three bromine atoms in the molecule, and (2) using antimony pentachloride as a chlorine source.

SUMMARY OF THE INVENTION

This invention pertains to a process for preparing bromine comprising reacting chlorine with ethylene dibromide the presence of a catalytic quantity of aluminum halide. The catalyst is selected from aluminum chloride, aluminum bromide, and aluminum chlorobromides. The process is conducted under substantially anhydrous conditions. This invention also pertains to use of bromine in the above process in order to shorten the induction period. In addition, it pertains to a procedure for isolation of products from the reaction mixture which entails a water wash to remove aluminum-containing material from the organic portion, drying the washed fraction with $H_2SO_4$, separation of the bromine-containing and $H_2SO_4$ layers, and distillation of bromine and ethylene dichloride from the dried layer.

Thus, this invention provides means for bromine generation from ethylene dibromide by a halogen exchange reaction with chlorine. Aluminum chloride is a preferred catalyst. Without being bound by any theory, the reaction is depicted as follows:

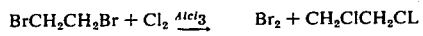

Conversions are high and the reaction is exothermic. Generally, there is an induction period. This can be shortened by addition of bromine and typically, the bromine can be from a previous reaction run.

In general, some aluminum halide catalyst is soluble in the reaction mass. This should be removed prior to product distillation for best results. Removal of aluminum-containing material can be accomplished by washing with water. Drying the washed fraction can be accomplished by contacting with $H_2SO_4$.

DESCRIPTION OF THE DRAWING

The FIGURE illustrates an initial charge of bromine increases the reaction rate and shortens the induction period. The increase in rate is shown by the greater slope of the curve from bromine plus $AlCl_3$ when compared to the curves for aluminum chloride alone. The decrease in induction period is shown by the shorter time lapse until a sharp slope change occurs, when the curve for $AlCl_3$ plus bromine is compared to the curves for $AlCl_3$ alone.

DESCRIPTION OF PREFERRED EMBODIMENTS

Because of the greater convenience and better reaction control, chlorine is preferably added to a mixture of aluminum halide and $BrCH_2CH_2Br$. However, other addition modes can be used. Thus, if desired, ethylene dibromide can be pressure injected into a vessel that contains chlorine under pressure and aluminum halide.

In the preferred addition mode, chlorine is added under the liquid surface at a rate such that the added chlorine does not bubble out of the resultant mixture throughout the reaction period. In other words, the rate of addition is lower than that which causes constant "breakthrough." Stated another way, the preferred mode of chlorine addition is at a rate at which substantially all the chlorine is absorbed upon contact by the reaction liquid.

Although avoidance of breakthrough, especially at beginning reaction stages, is preferred, it is not critical. Thus, breakthrough can be allowed to occur, especially in situations when advantageous to do so and where there are no untoward complications from the excess chlorine admitted. Thus, when using a series of reaction vessels, chlorine breakthrough can be used in some (or all) the vessels to achieve chlorine passage throughout the vessel series. Furthermore, as explained below, molar excesses of chlorine can be used. When this expedient is employed, breakthrough will occur, especially toward the end of the reaction period.

Summarizing, the rate of chlorine addition is not critical. However, for economical reasons, it is desirable to avoid chlorine wastage or unnecessary chlorine recovery and this can be accomplished by minimizing breakthrough. Furthermore, by controlling the rate of chlorine addition, the reaction rate is controllable; therefore, one can use the chlorine addition rate to minimize complications from too fast a reaction rate. Therefore, it is desirable to add chlorine at a rate at which all or substantially all the chlorine is absorbed by the reaction liquid. To save time, one can add the chlorine at the maximum rate at which complete or substantially complete absorption takes place. When an excess of chlorine is used, breakthrough can occur, especially at later reaction stages, and such breakthrough is expected. Likewise, some breakthrough may occur during the induction period.

To determine whether chlorine addition is proceeding at a desirable rate, the addition can be visually followed by observing through a transparent portion of the reaction vessel wall or by inspection of a bubbling or similar device which indicates flow from the reaction vessel.

In general, it is desirable to use at least one mole portion of chlorine per each mole portion of $BrCH_2CH_2Br$. In this way, both bromine atoms from an appreciable quantity of ethylene dibromide are recovered as elemental bromine. Using substantially less chlorine results in recovery of substantially less bromine, and when bromine recovery is the prime object, this may be economically unattractive. However, when the desired by-product is 1-bromo-2-chloroethane, then about one-half mole of chlorine per each mole of ethylene dibromide is used.

To obtain the maximum amount of bromine from ethylene dibromide, an excess of chlorine can be used. There is no real upper limit on the excess amount of chlorine and this is governed by such secondary considerations as economics. Generally, there is no real advantage to using a great excess of chlorine per mole of ethylene dibromide and in most instances, the reaction proceeds well when less excess chlorine is employed. Thus, to recover both bromines from ethylene dibromide as elemental bromine, preferably from 1.0 to 1.2 moles of chlorine are used per mole of ethylene dibromide, more preferably from 1.0 to 1.05 moles.

For the process to proceed at a suitable rate, a catalyst is used. Efficacious catalysts are aluminum halides. Of these, aluminum chloride, aluminum bromide, and aluminum chlorobromides are preferred. Of the three halogens per molecule in the chlorobromides, one or two are chlorine and the remainder are bromine. Of the halides mentioned, $AlCl_3$ and $AlBr_3$ are preferred with $AlCl_3$ being most preferred.

A catalytic amount of catalyst is employed. By catalytic amount is meant a quantity which gives a suitable reaction rate. The exact amount of catalyst is not critical. For example, there is no real upper limit on the amount of aluminum halide employed; this being governed by such secondary considerations as economics and reaction vessel size. Generally, it is preferable to employ the least amount of catalyst which allows the reaction to proceed at a utilizable rate. Thus, for example, aluminum chloride concentrations of about 0.5–2.0 weight per cent, preferably about 0.6 to 1.2 weight per cent based on the weight of the ethylene dibromide charged, are employed. Greater or lesser concentrations can be employed if desired. At a concentration of about 0.3 weight per cent of aluminum chloride, the reaction rate is rather slow.

When using another of the catalysts mentioned above, the concentration employed is about the same, taking into consideration differences in molecular weight and activity between the catalysts.

It has been discovered that bromine addition to ethylene dibromide before addition of chlorine is started, causes a reduction in the induction period. Only a small amount of bromine is required to achieve this effect. The bromine can be added in a number of ways, for example, the bromine can be part of a reaction heel from a previous run. In general, the amount of bromine is about 0.05 to 5 weight per cent, based on the amount of ethylene dibromide charged; more preferably between 0.5 and 0.9 weight per cent. As shown in the drawing, when bromine is employed it is not necessary to use as much aluminum halide catalyst. In other words, with a combination of operable amounts of a bromine and aluminum halide, a faster reaction rate was obtained when compared to that obtained when the same amount of aluminum chloride was used alone. There is no known real upper limit on the amount of bromine employed.

The process proceeds well at atmospheric pressure; however, greater or lesser pressures can be used if desired. In general, there is no real advantage to conducting the process under vacuum. As already referred to, the process can be conducted at superatomospheric pressure, say, up to 100 psi or higher, but utilizing a suitable reaction vessel pressurized with chlorine. Thus, one can initially add aluminum halide catalyst and chlorine to a pressure vessel and add ethylene dibromide reactant at a desired rate, using means which allow addition to take place against the pressure in the vessel. However, for this expedient, the equipment cost is greater. Summarizing, the reaction pressure is not critical and the process proceeds well under ambient or substantially ambient pressures.

Reaction temperature is not critical. A suitable temperature affords a reasonable reaction rate and does not cause an undesirable amount of product or reactant decomposition. The process proceeds at ambient temperatures, and slightly lower and slightly elevated temperatures can be used. Normally, slightly elevated temperatures are used to obtain a faster reaction rate. Thus, in general, a suitable temperature is between 30° and 100°C.; more preferably between about 40° and about 60°C., most preferably 45°–50°C.

After initiation, the reaction is exothermic, and cooling means can be employed to keep the reaction within the desirable temperature range. Furthermore, the temperature can be regulated to an appreciable extent by the chlorine addition rate. In general, chlorine is added over a period of from about 15 minutes to 5 hours; from one-half to one hour normally suffices.

To facilitate reaction, the reactants are efficiently contacted. In some instances, the amount of reaction mixture obtained by chlorine addition is insufficient. In such instances ancillary agitation means, such as stirring or rocking, can be utilized.

The reaction proceeds best in the absence of a substantial amount of water. In other words, better results are achieved under substantially anhydrous conditions. It is unnecessary to rigorously exclude water. Thus, chlorine and ethylene dibromide of normally available commerical grades can be employed. Furthermore, commercially available grades of anhydrous aluminum halides can be used. In general, the amount of water should not exceed 0.1 weight per cent, based on the weight of reactants and catalyst charged. However, it is to be understood that the reaction will tolerate a minor amount of water as indicated above.

There are two main products of the process, viz, bromine and an organic fraction. When chlorine and ethylene dibromide are reacted in at least substantially equally molar amounts, the organic fraction is largely ethylene dichloride. Bromine and ethylene dichloride can be recovered from the reaction zone by well known techniques, such as distillation. However, it has been found that recovery by distillation can lead to some decomposition of the organic portion and formation of hydrogen halide. This occurs when the distillation is conducted in the presence of aluminum-containing materials remaining after reaction. To avoid this problem, aluminum values are removed; this can be achieved by a water wash. The amount of water should be enough to substantially remove the aluminum substances. A minimum amount of water (3 mole $H_2O$/mole $AlCl_3$) gave a gummy mass of aluminum compounds and did not remove all of the aluminum. However, not as much decomposition occurred on distillation. Thus, it is desirable to wash the reaction mixture with an excess of water to remove at least most of the aluminum. There is no upper limit on the amount of water employed and in general from 5 to 60 weight per cent based on $Br_2$.ethylene dichloride is employed. However, as appreciated by a skilled practitioner, bromine is soluble in water and thus, the amount of water is kept within a range which removes enough aluminum for suitable distillation to take place, but which does not dissolve an undesirable amount of bromine product. For this reason, it is generally desirable to use from about 5 to about 20 weight per cent water; more preferably from 8 to 12 weight per cent.

Bromine extracted by the water wash is recoverable. It can be extracted with ethylene dichloride and the extracted portion in ethylene dichloride distilled with the dried layer discussed above. Alternatively, it can be extracted with ethylene dibromide and added to the next halogen interchange using the bromine as a portion or all of the bromine promoter employed to shorten the induction period.

The product distillation is enhanced when the fraction to be distilled is dried somewhat prior to distillation. A convenient drying means is treatment with concentrated sulfuric acid. In general, the sulfuric acid amount employed is from about 15 to about 125 ml, more preferably from 45 to 55 ml per 1200 g of reaction mixture employed. Recycling the $H_2SO_4$ to several batches may be carried out. Drying and use of $H_2SO_4$ to accomplish drying are not critical.

The following examples serve to illustrate the invention and not limit it. The product distillations reported in the examples were conducted in a eleven-plate bubble cap column. A more efficient column would give better separations. Typically, with the equipment employed in the examples, 81 per cent bromine recovery with 98 per cent assay was achieved.

EXAMPLE 1

To demonstrate the feasibility of the reaction, a system was set up to bubble chlorine through a mixture of ethylene dibromide and aluminum chloride. A mixture of 200 ml (~ 434 g) of ethylene dibromide and 5 g of aluminum chloride was stirred while chlorine was bubbled through. Chlorine was bubbled through at a slow rate for 2 hours. The reaction proceeded quite easily. It was necessary to cool the reaction mixture with an ice bath to keep the temperature below 50°. The mixture picked up 146.6 g in weight. This is about 90 per cent theory.

EXAMPLE 2

The procedure is the same as in the above example. A flask was charged with 430.8 g of ethylene dibromide and 5 g of aluminum chloride. The mixture was cooled with ice water and chlorine addition, with stirring, was started. The addition took ~45 minutes at which time 162.6 g of chlorine was added. The temperature rose to ~50° during the addition and was kept at 45°–50° until addition was complete. A 25.2 g and 2.00 g sample were taken for analysis ($Br_2$ and organics).

A simple distillation through a Vigreaux column was carried out. A cold trap was added to trap any bromine which was not condensed. The bromine distilled off in a range from 56° to 59°, pot temperature 67° to 96°. A total of 96 ml, 299.5 g, was collected plus 16.1 g in the cold trap. This is a total weight of 315.6 g of bromine.

The distillation was continued to remove the organics. Fumes were being evolved. A second cut of 6.5 g, b. p. 60°–81°, pot temperature 102°–104°, was taken. Ethylene dichloride was then distilled, b.p. 81°–86°, pot temperature to 125°. This third cut weighed 85.0 g. A fourth cut, b.p. 90°–105°, pot temperature to 132°C., weighing 28.7 g, was also taken. Distillation was stopped due to signs of increasng decomposition. The residue weighed 110.0 g and was a black liquid with carbonaceous solids present.

The total weight of material before distillation was 595.9 g, compared to 598.4 g, charged by weight. Taking into account the material used for samples, the isolated yield of bromine was about 90 per cent. The material balance is:

| Material in | g | Material out | g |
|---|---|---|---|
| EDB | 430.8 | $Br_2$ | 315.6 |
| $AlCl_3$ | 5.0 | Samples | 27.2 |
| $Cl_2$ | 162.6 | Distillation | |
| | | Cut 2 | 6.5 |
| | | Cut 3 | 85.0 |
| | | Cut 4 | 28.7 |
| | | Residue | 110.0 |
| | 598.4 | | 573.0 |

About 95.8 per cent of the charged material is accounted for. Analysis of the 2.00 g sample for bromine and chloride gave 1.407 g of bromide and 0.01 g of chloride. This corresponds to 2.62 moles of bromine in the reaction mixture which is above theory (theory is 2.3 moles of bromine) and to 3.0 g of chlorine. This suggests that the ethylene dibromide had been completely converted to bromine and ethylene dichloride.

EXAMPLE 3

The procedure of this example was employed to investigate the solubility of aluminum-containing species in the liquid portion of the reaction mixture.

To a mixture of 349.2 g of ethylene dibromide and 4.0 g of aluminum chloride was bubbled 131.8 g of chlorine over a 40 minutes period. The reaction mixture weighed 485.4 g (theory is 485.9 g). Analysis of the reaction mixture gave 320.2 g of bromine (theory is 297.1 g) and 6.9 g of chlorine. VPC analysis of the organic portion of the reaction mixture gave 93.2 weight per cent ethylene dichloride, 0.2 weight per cent ethylene dibromide and 0.5 weight per cent unknown.

The mixture was filtered to separate insolubles. The filtrate was sampled and analyzed for total aluminum. The insoluble aluminum residues on the filter were dissolved in hydrochloric acid and also analyzed for total aluminum. Based on these analyses, there was 0.45 g of aluminum in solution and 0.31 g of aluminum in the residues, total 0.76 g (theory is 0.81 g).

The filtrate was distilled by a simple overhead strip. Decomposition was noted during distillation as hydrogen halide was given off. The total distillate was 354 g, the liquid residue 63.5 g, the solid residue 2.7 g. The filrate weighed 431.8 g at the beginning of the distillation and 420.2 g were recovered.

EXAMPLE 4

This example demonstrates the use of a water wash prior to distillation in order to lessen the amount of decomposition during distillation.

The initial procedure was essentially the same as in Example 3. Quantities of reactants were 349.1 ethylene dibromide, 4.0 of aluminum chloride and 131.8 g of chlorine. Addition time was 1.5 hours. The temperature rose as high as 43°C. during chlorine addition. The reaction mixture weighed 483.0 g (theory is 484.9). A sample was taken and indicated that 300.6 g (101 per cent) of bromine were obtained. To the remaining solution was added 1.8 ml of water. The mixture was stirred for 15 minutes and filtered to give 463.1 g of filtrate. Distillation of the filtrate was carried out to obtain a fraction boiling up to about 80°C., at which time all the bromine had distilled. The distillate weighed at 415 g, the black pot residue weighed 39.5 g. Decomposition appeared to be much less than that achieved in the above experiments in which no water washed was carried out. The aluminum residues which had been filtered off were dissolved in hydrochloric acid and analyzed for total aluminum. This gave 0.306 g of aluminum (theory is 0.81 g).

EXAMPLE 5

This example demonstrates the use of a sulfuric acid treatment after water wash.

The reaction procedure was the same as in Example 4. Quantities used were 348.6 g of ethylene dibromide, 4 g of aluminum chloride and 131.6 g of chlorine. Chlorine addition took 1.33 hours and the maximum temperature reached was ~42°C. The reaction mixture weighed 482.3 g (theory is 484.2 g). A sample was taken for analysis. Bromine analysis gave a 98.2 per cent conversion and VPC gave 0.4 per cent of a low-boiling unknown, 96.4 per cent ethylene dichloride, 1.7 per cent 1-bromo-2-chloroethane and 0.1 per cent ethylene dibromide.

The reaction mixture was then stirred for 2 hours with 51.6 g of water. The bromine layer was separated. The aqueous layer, 43 ml., was analyzed for free bromine (0.0606 $Br_2$/ml) or 3.2 g of bromine in the aqueous wash. This is about 1.1 per cent of the total bromine. Aluminum analysis of the aqueous wash gave 0.69 g of aluminum or an 85 per cent recovery of charged aluminum. The bromine layer was shaken with 50 ml of concentrated sulfuric acid. The dry bromine layer was separated. It was then quickly distilled. There was no evidence of any decomposition during the distillation.

EXAMPLE 6

To a mixture of 433.7 g of ethylene dibromide and 5 g of aluminum chloride was bubbled 164 g of chlorine over a 1.1-hour period. The temperature was kept at about 40° through most of the reaction. The final reaction mixture weighed 601.6 g (theory 602.7 g). The mixture was stirred for 2 hours with 60.0 g of water. The water layer was removed. It weighed 68.4 g. The aqueous layer was analyzed for free bromine (4.35 weight per cent) and aluminum (1.28 weight per cent). This corresponds to an 86.7 per cent recovery of aluminum. The wet reaction mixture was then dried by mixing with 110.3 g of sulfuric acid. The bromine and sulfuric acid layers were separated. The bromine layer weighed 585.9 g, the sulfuric acid layer weighed 111.7 g. The material balance at this stage is:

|  | Material In (g) |  | Material Out (g) |
|---|---|---|---|
| Final Reaction Mixture | 601.6 | Dry Reaction Mixture | 585.9 |
| Water Wash | 60.0 | Water wash | 68.4 |
| $H_2SO_4$ | 110.3 | $H_2SO_4$ | 111.7 |
|  | 771.9 |  | 766.0 |

A 4.03 g sample was taken from the dry rection mixture. It was analyzed for bromine and chlorine. Bromine, 2.52 g and no chlorine were found. This corresponds to 366.4 g of bromine in the reaction mixture or ~100 per cent. VPC analysis of the organics gave 96.6 ethylene dichloride, 0.1 per cent ethylene dibromide and 0.5 per cent for three unknowns.

Distillation of the dry reaction mixture was carried out. Five cuts were taken during the distillation: Cut 1, b.p. 61°–66°, 235.9 g; Cut 2, b.p. 66°–74°, 163.0 g; Cut 3, b.p. 74°–82°, 85.2 g; Cut 4, b.p. 82°–83°, 73.2 g; Cut 5, b.p. 83°–84°, 14.6 g. The pot residue, 7.4 g, consisted of two layers of which the smaller, bottom layer was sulfuric acid. Cuts 1, 2, 3 and 4 were analyzed for free bromine. Found: Cut 1 — 199.9 g; Cut 2 — 107.6 g; Cut 3 – 26.9 g; and Cut 4 — 1.5 g.

| Distillation Material Balance | | | Bromine Material Balance | |
|---|---|---|---|---|
| Material In (g) | Material Out (g) | (g) | Bromine In (g) | Bromine Out |
| 581.9 | Cut 1 — 235.9 | | 363.9 | Cut 1 — 199.9 |
|  | 2 — 163.0 | | | 2 — 107.6 |
|  | 3 — 85.2 | | | 3 — 26.9 |
|  | 4 — 73.2 | | | 4 — 1.5 |
|  | 5 — 14.6 | | | |
|  | Residue 7.4 | | | |
| 581.9 | 579.3 | | 363.9 | 335.9 (92.3 per cent) |

VPC analysis of the organic portions of each fraction indicated they were primarily ethylene dichloride with small amounts of ethylene dibromide and 1-bromo-2-chloroethane present.

The aqueous water washes remaining after analysis from this experiment and Example 5 were combined to give 112.0 g of water liquid. This was extracted with 63.9 g of ethylene dichloride (~50 ml). The layers were separated and analyzed. The water layer weighed 106.6 g and contained 0.52 weight per cent $Br_2$, the ethylene dichloride layer weighed 66.7 g and contained 5.64 per cent $Br_2$. This corresponds to ~87 per cent of the bromine extracted in the ethylene dichloride layer.

EXAMPLE 7

The procedure is the same as Example 6. To the reaction mixture (432.0 g of ethylene dibromide, 2.5 g of aluminum chloride) was bubbled 163 g of chlorine over a 1.5-hour period. It took almost one hour to add the first 29 g of chlorine and only 0.5 hour to add the rest. Maximum temperature attained was ~48°. The reaction mixture weighed 594.5 g (theory, 597.5 g). Analysis of a sample indicated that the yield of bromine was 98.9 per cent. No chlorine was found. VPC analysis for organics gave 91.3 per cent ethylene dichloride, 3.2 per cent 1-bromo-2-chloroethane, 0.2 per cent ethylene dibromide and 0.8 per cent for five unknowns.

EXAMPLE 8

The flask was charged with 435.5 g of ethylene dibromide, 1.0 g of aluminum chloride and 10 ml of bromine. Chlorine addition was started. Rate of uptake of chlorine was very slow. After 0.67 hours only 14 g of chlorine had been added and chlorine was breaking through the mixture. A total of 64 g of chlorine was added over a 2.25 hour period. Much chlorine was breaking through. After this time it was noticed that a gas, presumably chlorine, was being given off by the reaction mixture. The reaction mixture weighed 497.3 g at the end. Analysis gave a yield of 13.6 per cent of bromine. There was also 10.2 g of chlorine in the mixture. VPC analysis of the organics gave 0.2 per cent ethylene dichloride, 20.1 per cent of 1-bromo-2-chloroethane, 74.4 per cent of ethylene dibromide, and 5.2 per cent unknowns.

Following the procedure of the above examples, aluminum bromide, aluminum chloride, $AlClBr_2$ and $AlBrCl_2$, and mixtures thereof can be used as the catalyst employing amounts of from 0.5 to 2.0 weight per cent based on the weight of ethylene dibromide charged. Similar results are obtained.

Also, similar results are obtained when the amount of chlorine charged is up to 1.1 or 1.2 moles per each mole of ethylene dibromide.

Similar results are obtained when the chlorine addition time is from 30 to 60 minutes and when the reaction temperature is from 40° to 60°C. and the entire reaction time is from 1 to 2 hours.

Similar results are obtained when the amount of water used in the water wash is from 5 to 20 weight per cent and the amount of concentrated $H_2SO_4$ used as a drying agent is from 15 to 125 ml per each 1200 g of reaction mixture.

EXAMPLE 9

A reaction flask was charged with 437.3 g of ethylene dibromide, 2.5 g of aluminum chloride, and 10 ml of bromine. Then 165 g of chlorine was bubbled in over a 0.9 hour period. The time for adding the first 22 g was 23 minutes, the rest of the chlorine was added over a 31-minute period. The reaction temperature at one time reached 65° accidentally but in the main it was at ~ 45°-50°. The reaction mixture at the end weighed 635.1 g (theory is 636.0 g). Analysis gave a yield of bromine of 99.6 per cent. No chlorine was found. VPC analysis gave 99.0 per cent ethylene dichloride, 0.1 per cent 1-bromo-2-chloroethane, 0.1 per cent ethylene dibromide and 1.6 per cent of six unknowns.

Similar results are obtained when the amount of bromine employed is from 0.5 to 0.9 weight per cent.

The data shown in the figure was obtained as follows:

In Example 6, the rate of chlorine addition to the reaction mixture is shown below:

| Time (min) | Temp. | g Cl$_2$ added |
|---|---|---|
| 0 | 25 | 0 |
| 28 | 39 | 31 |
| 38 | 43 | 61 |
| 47 | 43 | 96 |
| 56 | 41 | 131 |
| 66 | 43 | 164 |

In Example 7 the rate of chlorine addition is shown below:

| Time (min) | Temp. | g Cl$_2$ added |
|---|---|---|
| 0 | 25 | 0 |
| 22 | 33 | 5 |
| 54 | 30 | 29 |
| 64 | 45 | 59 |
| 70 | 48 | 89 |
| 77 | 42 | 119 |
| 83 | 43 | 149 |
| 86 | 42 | 163 |

In Example 9, the rate of chlorine addition is shown below:

| Time (min) | Temp. | g Cl$_2$ added |
|---|---|---|
| 0 | 27 | 0 |
| 23 | 50 | 22 |
| 31 | 46 | 52 |
| 37 | 45 | 82 |
| 43 | 45 | 112 |
| 49 | 42 | 142 |
| 54 | 38 | 165 |

Times and amounts of the above were used for the points on the curves.

We claim:

1. Process for preparing bromine comprising reacting chlorine with ethylene dibromide in the presence of a catalytic quantity of aluminum halide selected from aluminum chloride, aluminum bromide, and aluminum chlorobromides.

2. Process of claim 1 wherein the aluminum halide is aluminum chloride.

3. Process of claim 2 wherein the amount of aluminum chloride is about 0.5–2.0 weight per cent.

4. Process of claim 2 wherein the amount of aluminum chloride is about 0.6 to about 1.2 weight percent.

5. Process of claim 1 being conducted at from about 40° to about 60°C.

6. Process of claim 1 being conducted in the initial presence of an amount of bromine that lessens the reaction induction period.

7. A process of claim 1 wheren by-product ethylene dichloride is removed from the resultant reaction mixture by distillation, said distillation being preceded by water wash of said mixture, removal of the aqueous layer, drying the resultant wet residue with $H_2SO_4$, separation of the resultant bromine-containing and $H_2SO_4$ layer; said distillation being conducted on said bromine-containing layer.

8. Process of claim 6 wherein said initial amount of bromine is about 0.5 to 0.9 weight percent, and the catalyst is aluminum chloride.

9. A process of claim 1 being conducted with liquid ethylene dibromide, and being further characterized by introduction of said chlorine below the surface of said ethylene dibromide.

10. A process of claim 9 being conducted at a temperature of about 40°–60°C.

11. A process for preparing bromine in substantial accordance with the equation $$BrCH_2CH_2Br + Cl_2 \xrightarrow{AlCl_3} Br_2 + CH_2ClCH_2Cl$$

said process being conducted by introducing a gas consisting substantially of chlorine into a reaction zone initially substantially consisting of aluminum chloride and liquid ethylene dibromide such that said gas is introduced under the surface of liquid in said zone at a rate at which substantially complete absorption of said gas in said liquid takes place, said process being conducted at a temperature between about 40° and about 60°C, the amount of $AlCl_3$ being from about 0.6 to 1.2 weight percent based on the weight of ethylene dibromide.

12. Process of claim 11 being conducted in the initial presence of an amount of bromine that lessens the reaction induction period.

13. Process of claim 12 wherein the initial amount of bromine is about 0.5 to about 0.9 weight per cent.

14. A process of claim 12 wherein by-product ethylene dichloride is removed from the resultant reaction mixture by distillation, said distillation being proceeded by water wash of said mixture, removal of the aqueous layer, drying the resultant wet residue with $H_2SO_4$, separation of the resultant bromine-containing and $H_2SO_4$ layer; said distillation being conducted on said bromine-containing layer.

* * * * *